United States Patent [19]

Theis et al.

[11] Patent Number: 5,443,064
[45] Date of Patent: Aug. 22, 1995

[54] TRACHEOSTOMY TUBE WITH ADJUSTABLE NECK PLATE

[75] Inventors: Roger W. Theis, Valparaiso; Gerald E. Cabrera, Munster, both of Ind.

[73] Assignee: Bivona, Inc., Gary, Ind.

[21] Appl. No.: 217,445

[22] Filed: Mar. 24, 1994

[51] Int. Cl.⁶ .............................................. A61M 16/00
[52] U.S. Cl. ........................ 128/207.15; 128/DIG. 26; 128/207.14
[58] Field of Search ....................... 128/200.26, 207.14, 128/207.15, 207.17, 912, DIG. 26

[56] References Cited

U.S. PATENT DOCUMENTS

| | | | |
|---|---|---|---|
| 2,210,744 | 8/1940 | Winder | 128/207.15 |
| 2,908,269 | 10/1959 | Cheng | 128/DIG. 26 |
| 3,987,798 | 10/1976 | McGinnis | 128/DIG. 26 |
| 4,340,046 | 7/1982 | Cox | 128/207.15 |
| 4,516,293 | 5/1985 | Beran | 128/DIG. 26 |
| 4,530,354 | 7/1985 | Froilan | 128/207.17 |
| 4,683,882 | 8/1987 | Laird | 128/DIG. 26 |
| 4,825,861 | 5/1989 | Koss | 128/200.26 |
| 5,026,352 | 6/1991 | Anderson | 128/DIG. 26 |
| 5,054,482 | 10/1991 | Bales | 128/207.17 |
| 5,251,616 | 10/1993 | Desch | 128/912 |

Primary Examiner—Edgar S. Burr
Assistant Examiner—Aaron J. Lewis
Attorney, Agent, or Firm—Emrich & Dithmar

[57] ABSTRACT

A tracheostomy tube includes a substantially straight tube of a highly flexible material and having a wire reinforcement and a neck plate which is adapted for sliding movement axially of the tube between the proximal and distal ends of the tube. The neck plate includes a split collar elastic member which extends around the tube. The split collar member includes a tab at one end which is stretched to overlie the other end of the collar and can be locked to the other end of the collar by a pin and hole arrangement to fixedly secure the neck plate to a predetermined position on the tube.

9 Claims, 1 Drawing Sheet

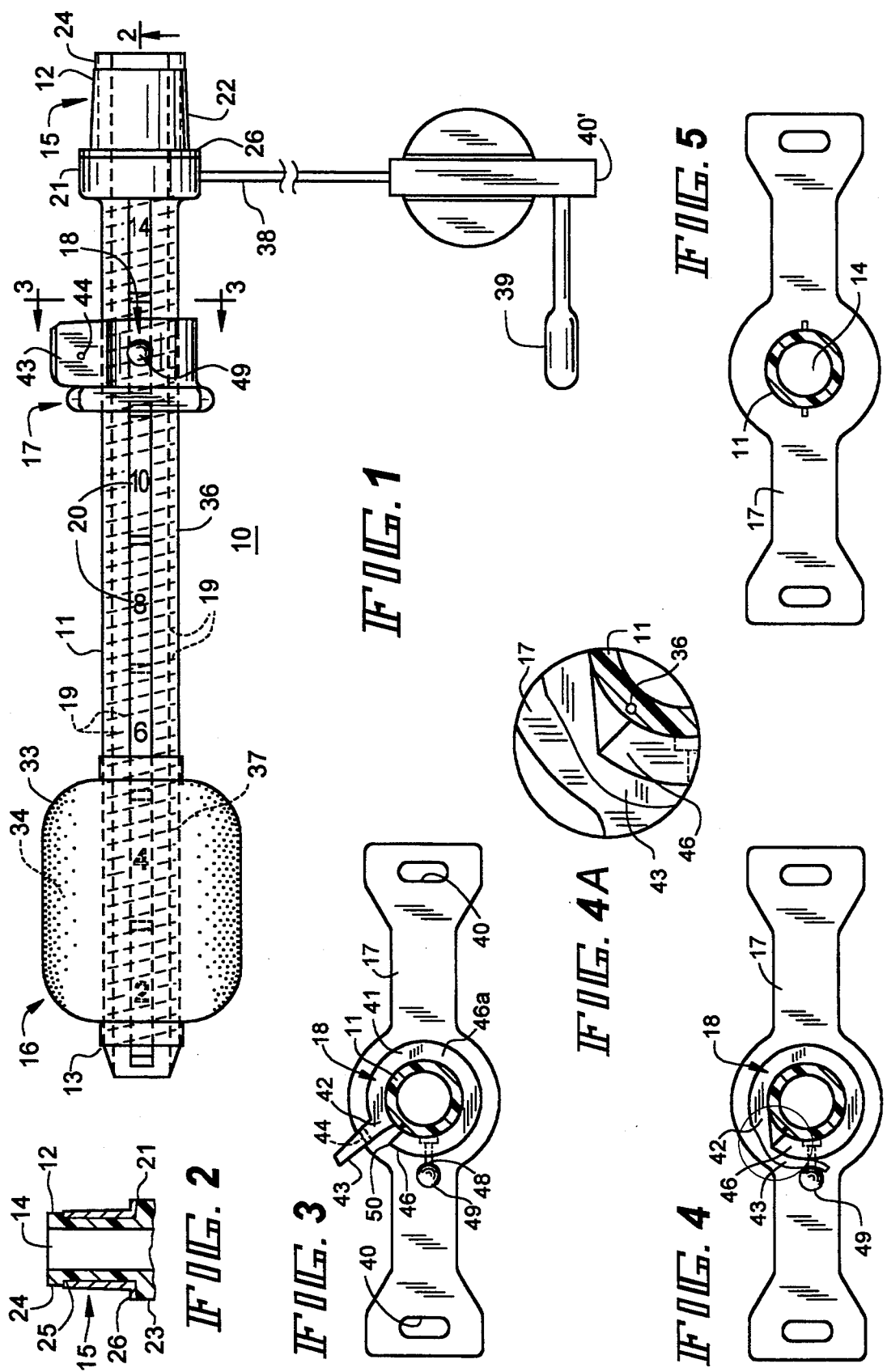

TRACHEOSTOMY TUBE WITH ADJUSTABLE NECK PLATE

BACKGROUND OF THE INVENTION

This invention relates to tracheostomy tubes, and more particularly, to a tracheostomy tube having an adjustable neck plate.

Tracheostomy tubes are used to provide a means of airway management, for example, the bypass supply of oxygen or air to a patient when an obstruction occurs within the larynx or the pharynx area. Typically, the tracheostomy tube is inserted through an incision which is made in the patient's neck below the obstructed area. After the tube has been positioned in the trachea, the tube is held in place by a neck plate which includes slots for receiving a strap for tying the tube to the patient's neck. For existing adjustable tracheostomy tubes, once the tube has been fitted, the neck plate can adjust only for thickness of the neck of the patient. Fixed neck plate tracheal tubes cannot be adjusted. If a patient develops a tracheal malasia due to poor cuff maintenance or other complications, changing of the cuff site becomes critical. Under such circumstances, the care giver either must order a "custom" made product or attempt to alter the tube to meet the need, neither of which is a satisfactory solution from the patient discomfort standpoint.

Conventionally, the proximal end of the tracheostomy tube includes a connector for connection to a supply line which is connected to a ventilator or to a source of oxygen or air. It is important that the connector be allowed a degree of rotational freedom relative to the tube so that normal movement of the patient relative to the supply line is tolerated without exerting any torque forces on the tube. Accordingly, most tracheostomy tubes have swivel connectors fixedly connected thereto to facilitate connection to the supply line. Because the swivel connectors are fixedly mounted to the tube, they cannot be removed or replaced when the need arises.

Known tracheostomy tubes generally are made of a rigid material and are formed with a preset curvature, typically in the range of 70° to 90°. The curvature of the tube is somewhat difficult to alter because of the material of which the tube is made. In cases of abnormal tracheal anatomy, the shaft will kink or otherwise push on the tracheal wall, causing patient discomfort and in some cases damage or injury to the trachea. Indeed patient discomfort caused by prolonged cuff-tracheal pressure generally may result in patient injury. Moreover, the tubes may be made of a plastic material which is not radiopaque so that proper positioning of the tube can be determined only by external observation.

Some tracheostomy tubes that are currently available include mating inner and outer cannulas which are interconnected through the use of rigid flanges on a connector collar that is permanently formed on the outer tube or cannula. The inner cannula has associated therewith a connector collar having a knurled cap which is adapted to be tightened onto the connector collar on the outer cannula. Examples of such locking tracheal tubes are disclosed in U.S. Pat. No. 4,304,228, which was issued to William Depel, U.S. Pat. No. 4,009,720, which was issued to Norman C. Crandall and U.S. Pat. No. 3,659,612, which was issued to Donald P. Shiley. In these prior art tracheal tubes, the neck plates are integral with the connector collar and, as such, the neck plates are not adjustable axially of the tube.

SUMMARY OF THE INVENTION

The present invention provides a tracheostomy tube having an adjustable neck plate which is repositionable axially of the tube. The neck plate is maintained in place by a locking means in the form of a collar which is secured to the tube by an elastic member portion that is adapted to be hooked over onto a protruding pin extending form the body portion of the locking collar. The neck plate and locking collar means enables axial adjustment of the position of the neck plate along the length of the tube to allow relocation of the cuff site as well as adjustments to adapt for the thickness of the neck of the patient. This permits the cuff site to be moved when required without the need for obtaining a custom made tube. Another advantage of the locking arrangement provided by the present invention is that a direct visual indication is provided as to whether or not the device is locked. Also, the combination neck plate and locking collar is characterized by ease of cleaning and is made of material that is autoclavable.

Further in accordance with the invention, the tube includes a flexible, wire reinforced shaft which permits the tracheostomy tube to conform to anatomical variations without patient discomfort. The wire reinforcement of the shaft permits bending of the tracheostomy tube but renders the tube resistant to kinking.

Additionally, in accordance with the present invention, the locking of the axially adjustable neck plate and collar means to the tube results in a firm and fixed attachment of the neck plate to the tube without compressing the flexible, wire reinforced tube.

The visual indicator located on the collar means provides alignment of the collar means with respect to the inflation lumen that is incorporated in the wall of the tube to prevent stress on and the collapse of the inflation lumen when the collar means and neck plate is locked to the tube.

The invention consists of certain novel features and structural details hereinafter fully described, illustrated in the accompanying drawings, and particularly pointed out in the appended claims, it being understood that various changes in the details may be made without departing from the spirit, or sacrificing any of the advantages of the present invention.

DESCRIPTION OF THE DRAWINGS

FIG. 1 is a top plan view of a tracheostomy tube provided by the present invention;

FIG. 2 is a section view taken along the line 2—2 of FIG. 1;

FIG. 3 is a section view taken along the line 3—3 of FIG. 1 showing the neck plate and locking collar means in the open position;

FIG. 4 is a view similar to that of FIG. 3, but showing the neck plate and locking collar means in the closed position about the tube;

FIG. 4A is an enlarged view of a portion of FIG. 4; and

FIG. 5 is a rear plan view of the neck plate and locking collar means.

DESCRIPTION OF A PREFERRED EMBODIMENT

Referring to FIGS. 1 and 2, the tracheostomy tube 10 provided by the present invention includes an elongated tube 11 having a proximal end 12, a distal end 13 and a bore 14 therethrough. The tube 11 has a connector 15 at its proximal end 12, a cuff 16 at its distal end 13 and a neck plate 17 which is secured to the tube 11 by a locking collar member or means 18. The tube 11 is made of an extremely flexible material and includes wire reinforcement 19, preferably spirally wound in the wall of the tube, so that the tube 11 is kink resistant and is able to conform to anatomical variations without patient discomfort. The wire reinforcement 19 is radiopaque and thus aids in verifying the positioning the tube using x-ray or other imaging devices. Preferably, the tube 11 has markings 20 along its length for indicating the depth of insertion of the tube into a patient's trachea.

The connector 15 is defined by an enlarged portion 21 having a swivel connector 22 of a rigid plastic material mounted thereon and adapted for rotation relative to the tube 11. The enlarged portion 21 is generally cylindrical in shape and has an inner diameter that corresponds to the bore 14 of the tube 11 and an outer diameter that is greater than the outer diameter of the tube 11. The enlarged portion 21 has an annular flange 23 at its distal end and a annular shoulder 24 at its proximal end, defining an annular groove or channel 25 in the enlarged proximal end portion of the tube 11. The swivel connector 22 is a sleeve-like member which is located in the channel 25 disposed between and held in place by the flange 23 and shoulder 24 with its flange 26 engaging the flange 23 of the enlarged end portion and the end 27 or the connector 22 engaging the shoulder 24. The shoulder 24 is deformable to permit removal of the swivel connector 22.

The cuff member 16 is located near the distal end 13 of the tube 11 for sealingly engaging the inside of the trachea of a person into which the tube has been inserted. The cuff 6 includes a normally expanded balloon cuff embodying an air impervious cover 33 which is normally resiliently maintained in an expanded condition by a resilient member 34 mounted therein, the resilient member being made of a suitable material, such as sponge rubber. The cuff has an inflation lumen 36, preferably, extending within the wall 11a of the tube 11 (FIG. 4A). One end 37 of the inflation lumen 36 is connected to the interior of the cuff and the other end 38 of the tube 36 extends through the flange 23 and outwardly away from the tube 11. The end 38 is fitted with a plug 39 for temporarily closing the opening 40 in the end 38 of the tube.

The cuff 16 is normally maintained in an inflated condition by the resilient member 34 and when it is desired to insert the tube into the trachea of a patient, air is withdrawn from the interior of the cover by applying suction to the end 38 of the inflation lumen 36, thereby collapsing the cuff 16. The plug 39 is inserted into the opening 40' to seal the tube 36 temporarily. After the tracheostomy tube 10 has been located at the proper position in the trachea of the patient, the plug is withdrawn to thereby permit the cuff 16 to expand into sealing engagement with the inner surface of the trachea of the patient, the resilient material affording a soft, yieldable pressure for effecting a sealing engagement.

The neck plate 17 is positionable near its proximal end 13 of the tube 11. In accordance with the present invention, the neck plate is adjustable axially of the tube 11 to be repositionable in a direction toward and away from the patient's neck. Accordingly, the cuff site and associated cuff member 16 is repositionable within the patient's trachea because the tube 11 is wire reinforced flexible material which conforms to the anatomical variations of the patent's trachea and because the neck plate 17 and associated locking means 18 is adjustable axially of the tube.

Referring to FIGS. 1 and 3, the neck plate 17 is a flat, plate-like member formed integrally with a split collar 18 which secures the neck plate 17 to the tube 11. As shown in FIG. 3, the split locking collar 18 is secured to or made integral with the neck plate 17 by having the end portion 46 of the split annular band 41 secured to or made integral with the neck plate 17. The split annular band 41 is secured to or made integral with the neck plate approximately one-half the circumferential distance 46a between end portion 46 and first end 42. This structure permits the split annular band 41 portion of the locking collar 18 and the neck plate 17 to be secured to the tube, as will hereinafter be described. The neck plate has apertures 40 at each end for receiving a strap for securing the neck plate to a patient's neck.

The neck plate 17 is preferably composed of a relatively stiff elastomeric material and the locking collar 18 is preferably composed of a soft more elastic material. The elastic modulus elastomeric material of the locking collar was chosen to optimize its locking characteristics and recovery characteristics when the locking collar is manipulated between the closed or locked condition to the open or unlocked condition.

The visual indication on the collar means provides alignment of the collar means with respect to the inflation lumen that is incorporated in the wall of the tube to prevent stress on and the collapse of the inflation lumen when the collar means and neck plate is locked to the tube.

The locking collar 18, which locks the neck plate to the tube 11 at a desired location along the length of the tube, includes a split annular band 41 having a first end 42 with an elastic tab 43 which projects outwardly from the end 42 in a direction substantially normal to the band at end 42. The tab 43 has an aperture 44 therethrough. The band 41 has a second end 46 with an outwardly directed or protruding pin 48 near end 46. The end of the pin 48 in formed with a bulbous head 49. As shown in FIG. 3, the split locking collar 18 is secured to or made integral with the neck plate 17 by having the end portion 46 of the split annular band 41 secured to or made integral with the neck plate 17. The split annular band 41 is secured to or made integral with the neck plate approximately one-half the circumferential distance 46a between end portion 46 and first end 42. This structure permits the split annular band 41 portion of the locking collar 18 and the neck plate 17 to be secured to the tube, as will hereinafter be described. The locking collar 18 allows securing to the tube 11 by hooking the elastic tab 43 over and onto the protruding pin 48. This is done simply by pulling the tab onto the pin. This can be done with one hand by gripping the tab between the thumb and forefinger. Locking of the neck plate does not place stress on the tube after it is in place in the patient's trachea by virtue of the wire reinforced flexible tube. An important advantage of the locking arrangement provided by the present invention is that a direct visual indication is provided as to whether or not the device is locked, as can be seen by comparing FIGS. 3 and 4. The collar is not removable from the tube 11 when the collar is in the open or unlocked condition, but the neck plate and locking collar may be manipulated to offer greater visual advantage for cleaning, as compared to existing prior art structures.

The neck plate 17 is characterized by ease of cleaning. The integral neck plate 17 and collar are made of material that is autoclavable.

The collar 18 has an open or unlocked condition illustrated in FIGS. 1 and 3 and a closed condition which is illustrated in FIG. 4. In the open or unlocked condition, there is a gap 50 between the ends 42 and 46, allowing the collar and the neck plate attached thereto to axially slide along the outer surface of the tube 11. This sliding movement is facilitated by depressing or rotating the end 42 in a direction away from end 46, providing a maximum inner diameter for the collar. To secure the collar and the neck plate to the tube 11, the tab 43 is grasped between the thumb and forefinger and pulled, stretching the tab 43 so that the aperture 44 overlies the pin 48. As the tab is stretched, the aperture 44 is elongated, allowing the pin to pass through the aperture to the lock condition, as illustrated in FIG. 4. In the locked condition, the end 42 is in close proximity to end 46 to provide a minimum inner diameter for the collar 18, so that the collar is tightened against the outer surface of the tube 11, preventing axial sliding movement of the collar with respect to the tube. This movement preventing function is enhanced by the fact that the collar and the tube 11 are made of the same elastic material and the engaging surfaces do not lend themselves to relative movement.

When the neck plate 17 and locking collar means 18 is in the locked condition or closed position, the gap 50, provided by the overlapping of tab 43 over end 46 to engage pin 49, and between the ends 42 and 46, is positioned and aligned to be adjacent thereby preventing the inflation lumen 36 within the wall of tube 11. This result is achieved by aligning the end portion 46 of the split annular band 41 adjacent to the inflation lumen 36 such that when the locking collar is in the locked condition, the gap 50 is aligned over the inflation lumen 36, the portion as shown in FIG. 4A. However, it is within the scope of the present invention that the positioning of the gap 50 over the inflation lumen 36 may also be achieved by separately marking and locating the marking on the collar member with respect to the tube by predeterminely positioning the inflation lumen 36 within the wall of the tube 11 adjacent the markings 20 to provide alignment and overlap of the gap 50 with respect to the inflation lumen.

Although illustrated as being a foam cuff, the cuff 16 may be an air inflatable cuff or other known types of cuffs or the tracheostomy tube may be cuffless. Moreover, although the tracheostomy tube has been described with reference to an application for insertion through an incision in the neck of a patient, the principles of the invention are applicable to endotracheal tubes and other types of tubes, such as those having inner and outer cannulas, for example.

We claim:
1. A tracheostomy tube comprising:
a tube having a wall, a proximal end, a distal end and a bore therethrough, said tube having a predetermined outer wall diameter between said proximal and distal ends;
neck plate means including a neck plate and a collar portion, said neck plate being adapted to be secured to the neck of a patient, said collar portion being adapted for sliding movement axially of said tube for repositioning said neck plate between said proximal and distal ends of said tube; and
said collar portion having first and second ends and including a tab portion defined at said first end and a pin defined at said second ends, said tab portion having an aperture for receiving said pin, said collar portion fitting around said tube and said pin being structurally arranged so that the inner diameter of said collar portion is engageable with the outer diameter of said tube when said tab portion is locked to said pin, with said tab portion being made of an elastic material thereby permitting said tab portion to be stretched to locate said aperture in overlying relationship with said pin, thereby securing said neck plate at a desired position axially of said tube.

2. The tracheostomy tube according to claim 1, wherein said pin is formed on one end of said collar and said tab portion is formed on the other end of said collar.

3. The tracheostomy tube according to claim 2, wherein said pin and said tab portion are formed integrally with said collar and said neck plate is formed integrally with said collar.

4. The tracheostomy tube according to claim 2 wherein said tube includes a cuff member located adjacent said distal end and an inflation lumen positioned in the wall of said tube communicating with said cuff member, with said tab portion of said collar portion providing a gap positioned over said inflation lumen positioned in the wall of tube to prevent the collapse of said inflation lumen when said tab portion is locked to said pin.

5. The tracheostomy tube according to claim 1, wherein said tube is made of a substantially straight flexible material and includes a wire reinforcement within said wall which permits horizontal and vertical adjustment of the tracheostomy tube.

6. The tracheostomy tube according to claim 5 wherein said tube includes markings thereon for visual verification that said neck plate means has not moved from said desired position.

7. The tracheostomy tube according to claim 1, including a swivel connector mounted on said proximal end of said tube, said proximal end of said tube having a flange and a shoulder for maintaining said swivel connector in place on said tube, said shoulder being deformable to permit removal of said swivel connector.

8. The tracheostomy tube according to claim 1, wherein said tube is comprised of a substantially straight flexible material.

9. The tracheostomy tube according to claim 1, wherein said tube includes a wire reinforcement within said wall.

* * * * *